United States Patent
Lee et al.

(10) Patent No.: US 8,410,453 B2
(45) Date of Patent: Apr. 2, 2013

(54) ULTRAVIOLET STERILIZER HAVING VIBRATION-PROOF FUNCTION

(75) Inventors: Soo-Tae Lee, Busan (KR); Tae-Sung Pyo, Busan (KR); Su-Kyu Lee, Busan (KR)

(73) Assignee: Panasia Co., Ltd., Busan (KR)

( * ) Notice: Subject to any disclaimer, the term of this patent is extended or adjusted under 35 U.S.C. 154(b) by 18 days.

(21) Appl. No.: 13/000,980

(22) PCT Filed: Jun. 18, 2010

(86) PCT No.: PCT/KR2010/003969
§ 371 (c)(1),
(2), (4) Date: Dec. 22, 2010

(87) PCT Pub. No.: WO2011/155655
PCT Pub. Date: Dec. 15, 2011

(65) Prior Publication Data
US 2011/0303855 A1    Dec. 15, 2011

(30) Foreign Application Priority Data
Jun. 11, 2010    (KR) .................. 10-2010-0055638

(51) Int. Cl.
*A61L 2/10*    (2006.01)
(52) U.S. Cl. .............. 250/455.11; 250/454.11; 250/436; 422/22; 422/24
(58) Field of Classification Search .............. 250/455.11, 250/454.11, 435, 436, 504 R; 422/22, 24
See application file for complete search history.

(56) References Cited

U.S. PATENT DOCUMENTS

| | | | | |
|---|---|---|---|---|
| 4,563,286 A | * | 1/1986 | Johnson et al. | ............... 210/721 |
| 5,471,063 A | | 11/1995 | Hayes et al. | |
| 6,071,473 A | * | 6/2000 | Darwin | ........................... 422/20 |
| 6,634,902 B1 | * | 10/2003 | Pirovic | ........................... 439/337 |
| 2006/0231770 A1 | * | 10/2006 | Snowball | .................. 250/432 R |
| 2007/0241288 A1 | | 10/2007 | Wang | |
| 2008/0265775 A1 | | 10/2008 | Schiene et al. | |
| 2008/0295271 A1 | * | 12/2008 | Perunicic | ...................... 15/246.3 |
| 2012/0051977 A1 | * | 3/2012 | Boodaghians et al. | ........ 422/117 |

FOREIGN PATENT DOCUMENTS

| | | |
|---|---|---|
| KR | 20-0399286 | 10/2005 |
| KR | 10-0739045 | 7/2007 |
| WO | WO 95/19188 | 7/1995 |

* cited by examiner

*Primary Examiner* — Kiet T Nguyen
(74) *Attorney, Agent, or Firm* — Rabin & Berdo, P.C.

(57) ABSTRACT

Disclosed herein is an ultraviolet sterilizer having a vibration-proof function. The ultraviolet sterilizer includes an ultraviolet sterilization unit. The ultraviolet sterilization unit has an inlet through which ballast water is drawn thereinto, an outlet through which the ballast water is discharged therefrom, and an ultraviolet lamp located between the inlet and the outlet. The ultraviolet lamp applies ultraviolet rays to the ballast water. The ultraviolet sterilizer further includes a cap which supports each of the opposite ends of the ultraviolet sterilization unit, and a shock absorption unit which is elastically compressed at a first end thereof by the cap while a second end thereof compresses an end of the ultraviolet lamp. Thereby, even if the ultraviolet sterilization unit vibrates, the sleeve pipe or the ultraviolet lamp can be prevented from being damaged, and explosive gas which may cause the ultraviolet sterilizer to explode is also prevented from entering the cap.

10 Claims, 14 Drawing Sheets

【Figure 1】
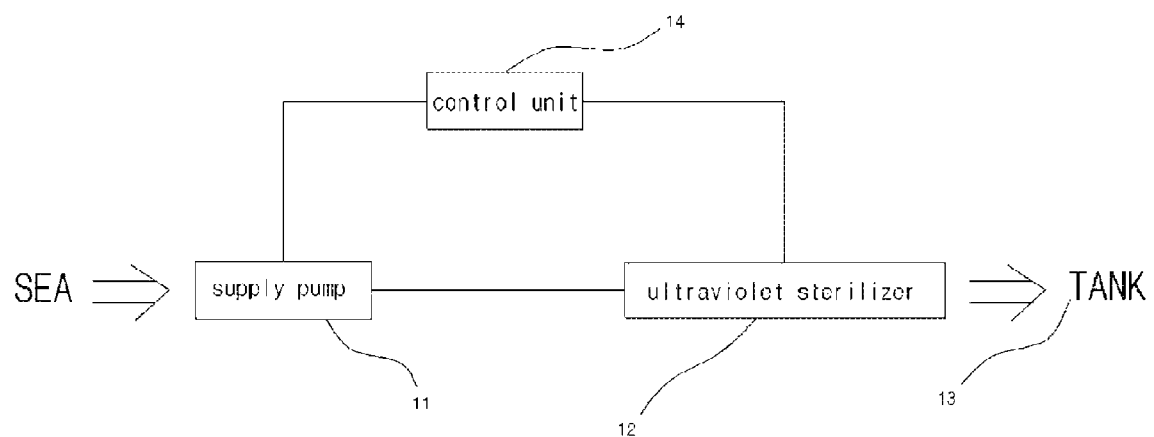

【Figure 2】
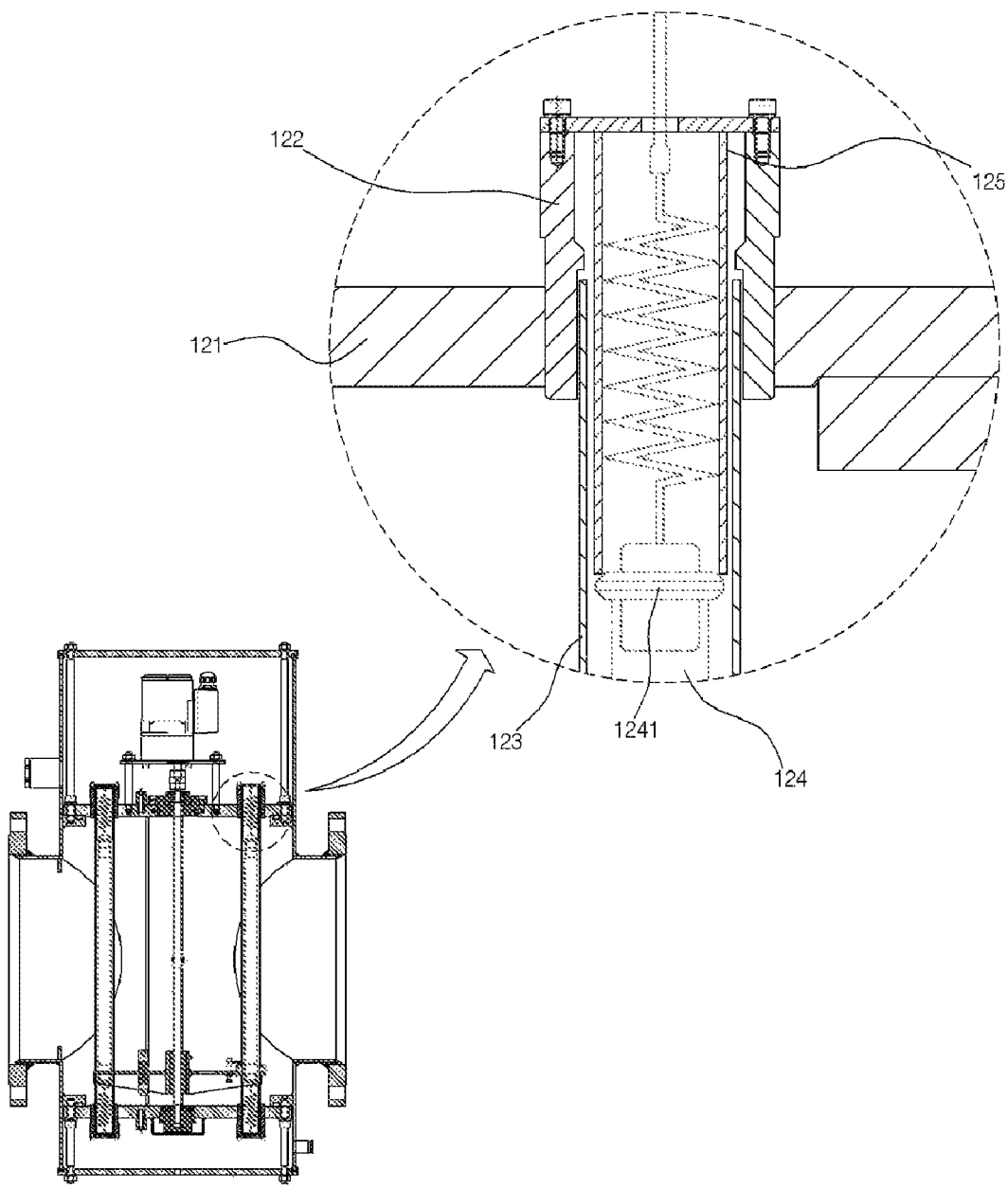

【Figure 3】
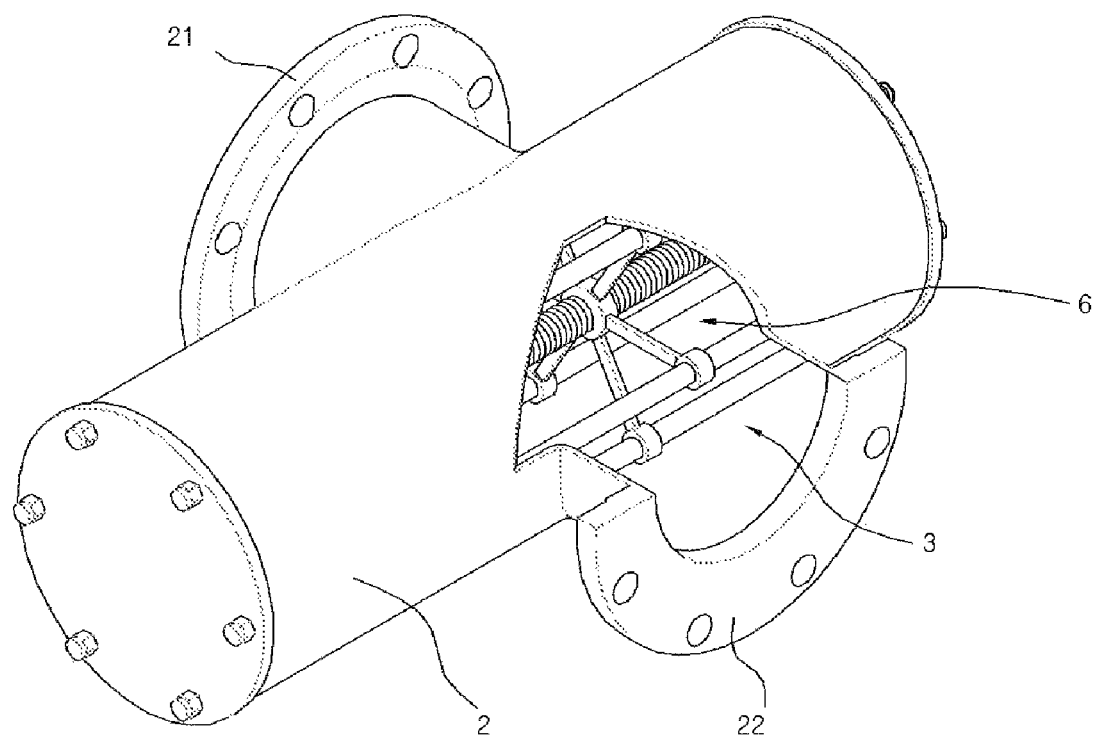

[Figure 4]
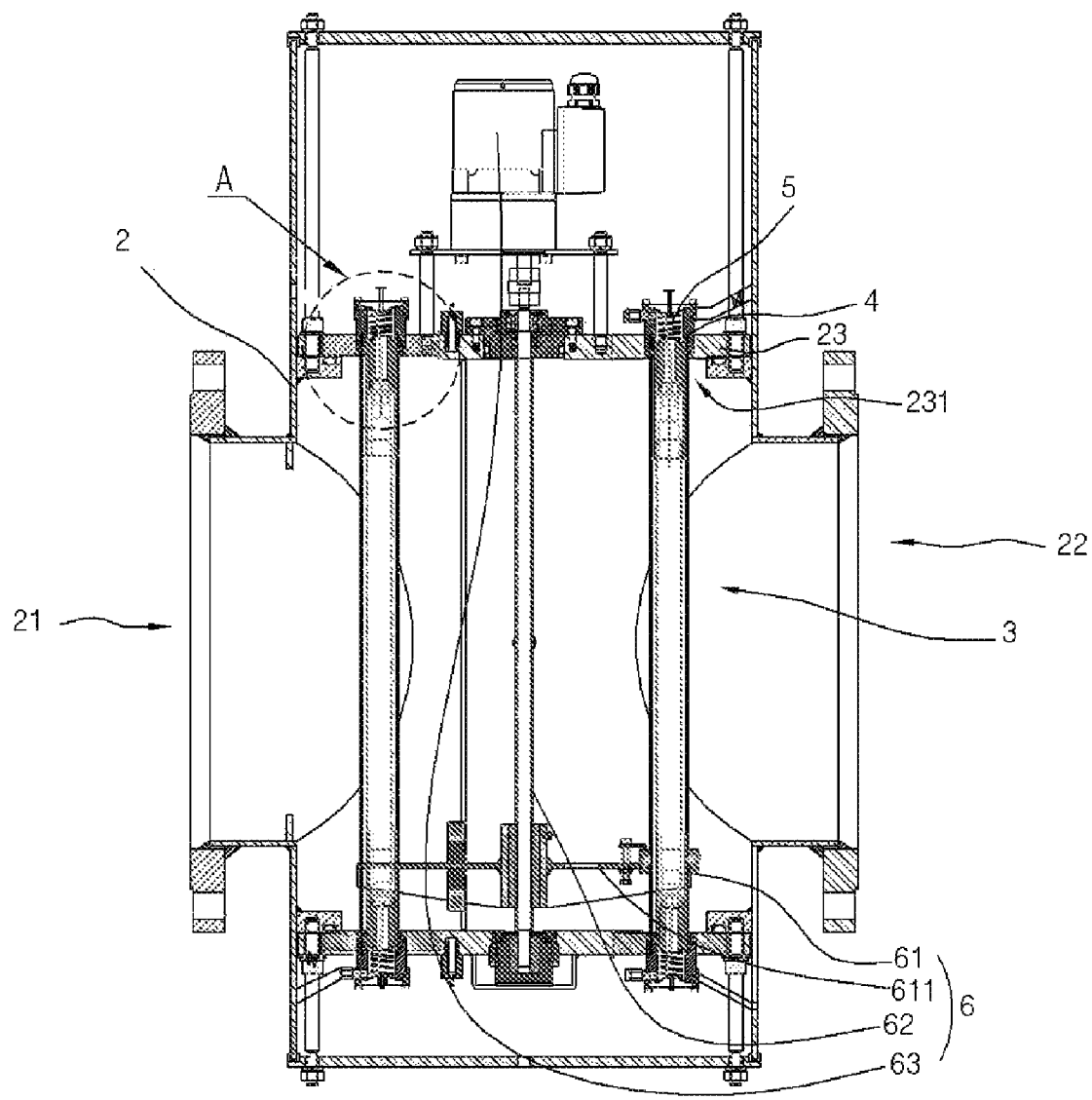

[Figure 5]
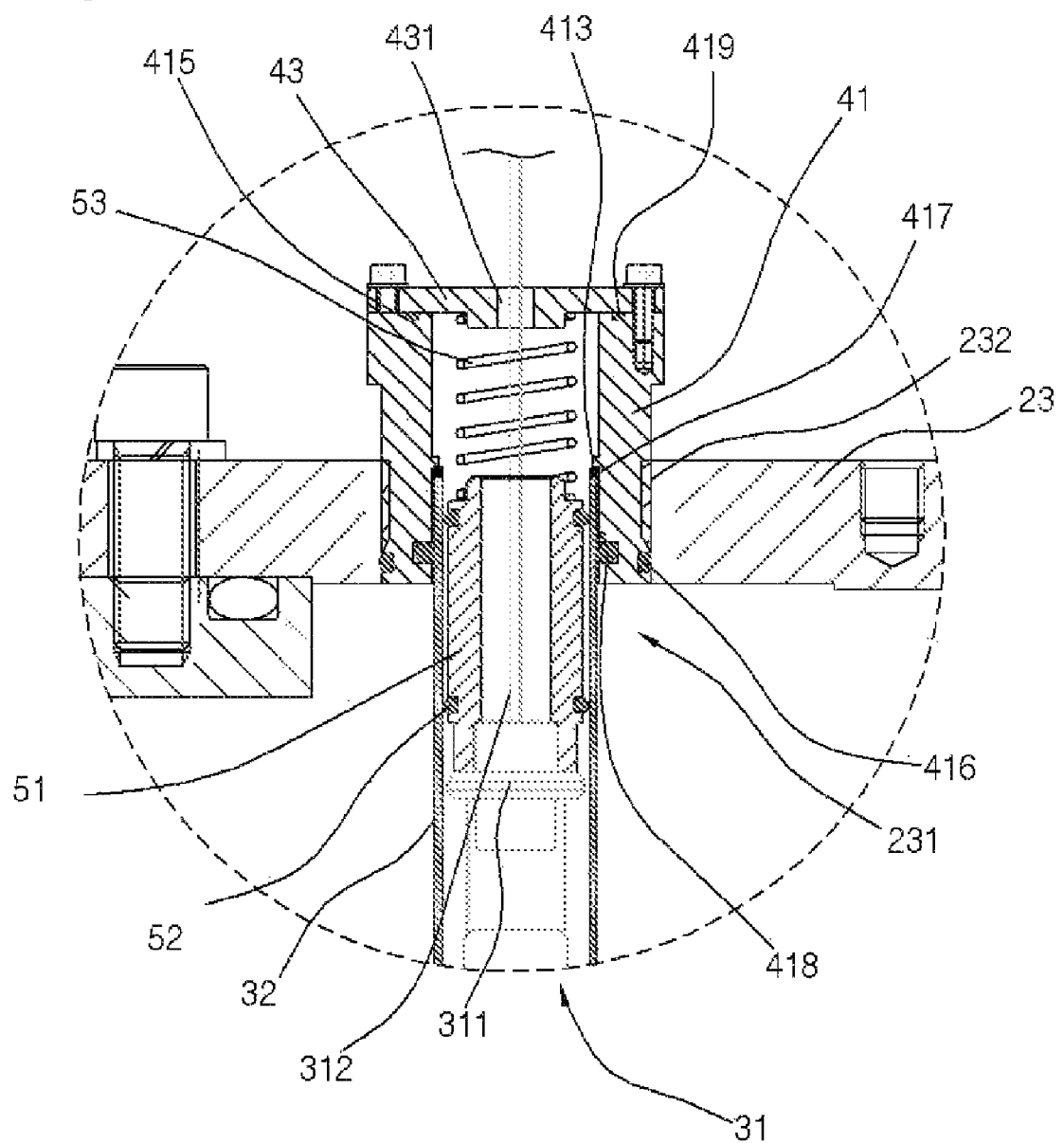

【Figure 6】
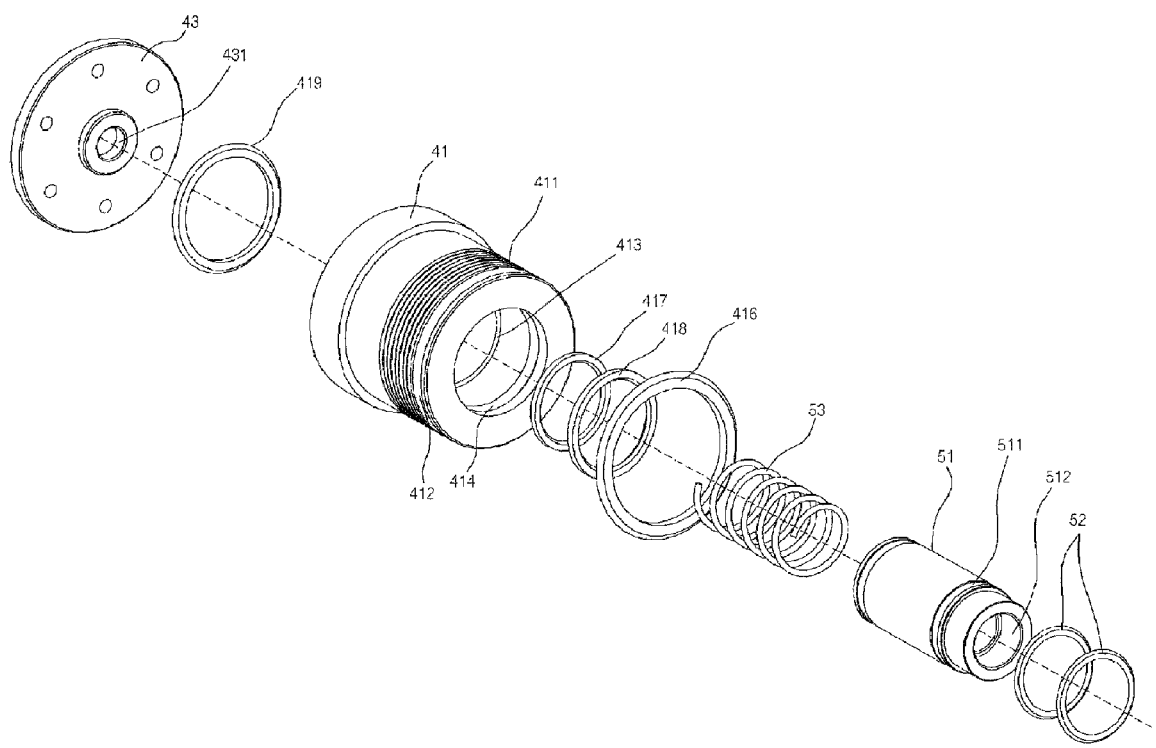

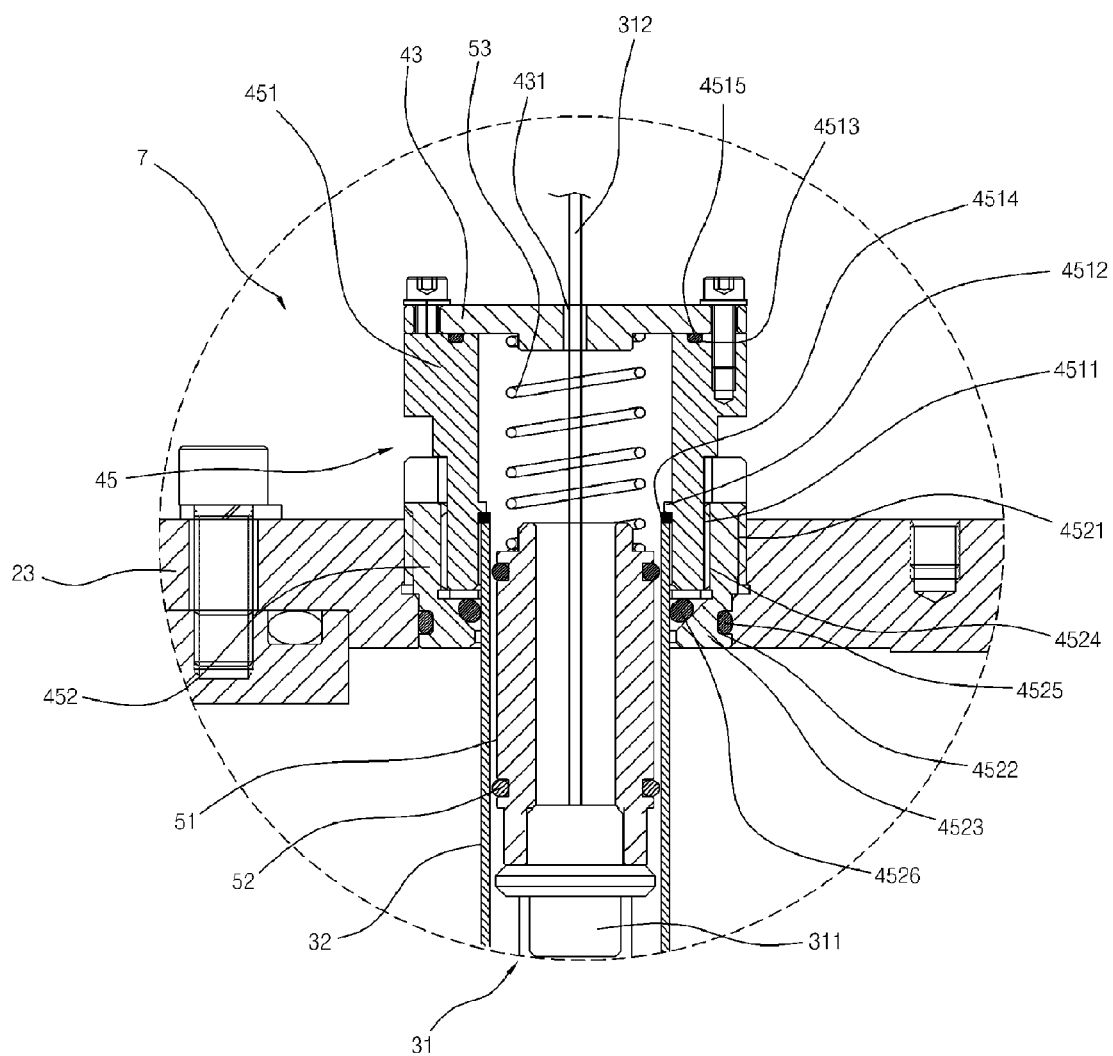
[Figure 7]

[Figure 8]
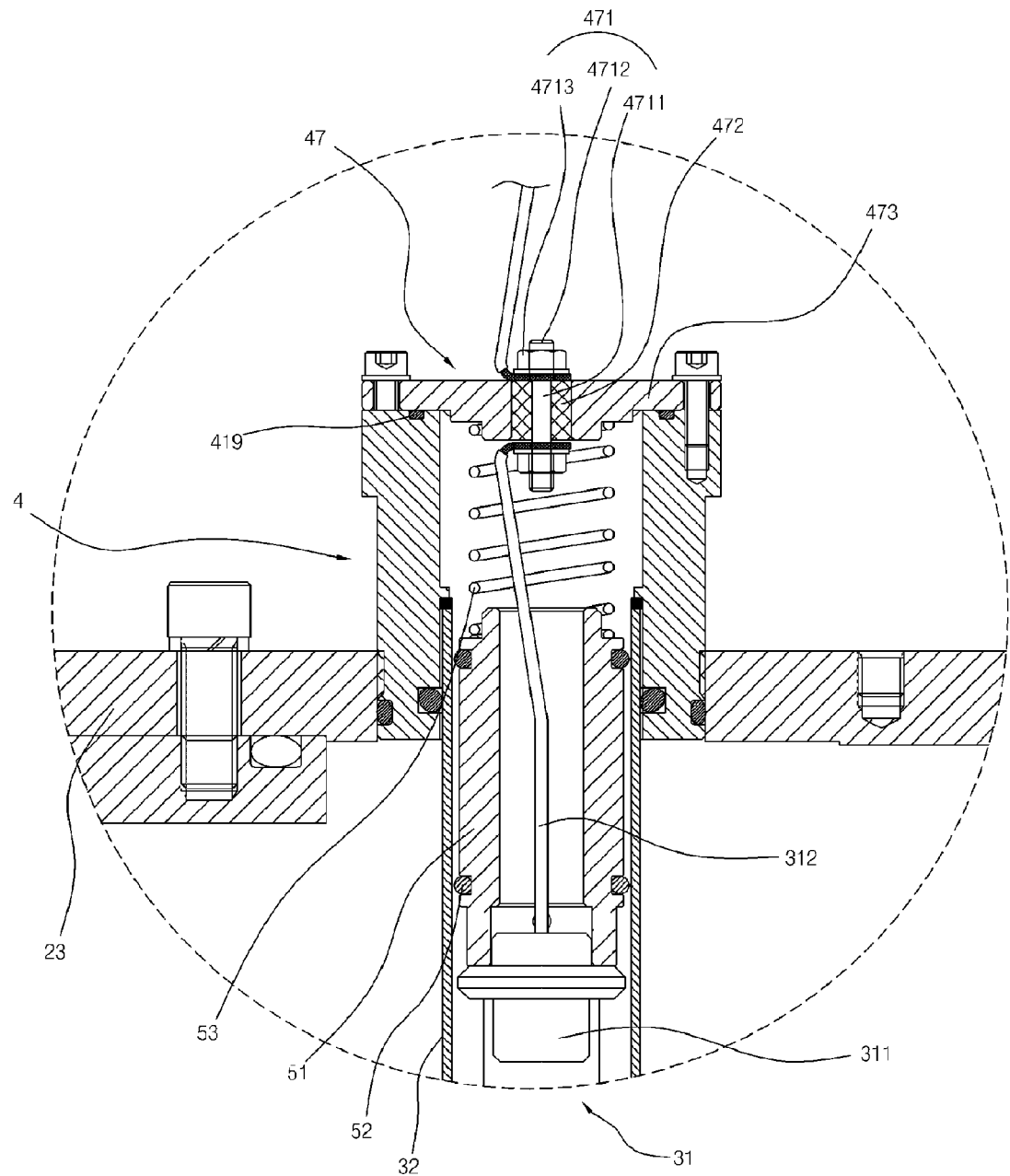

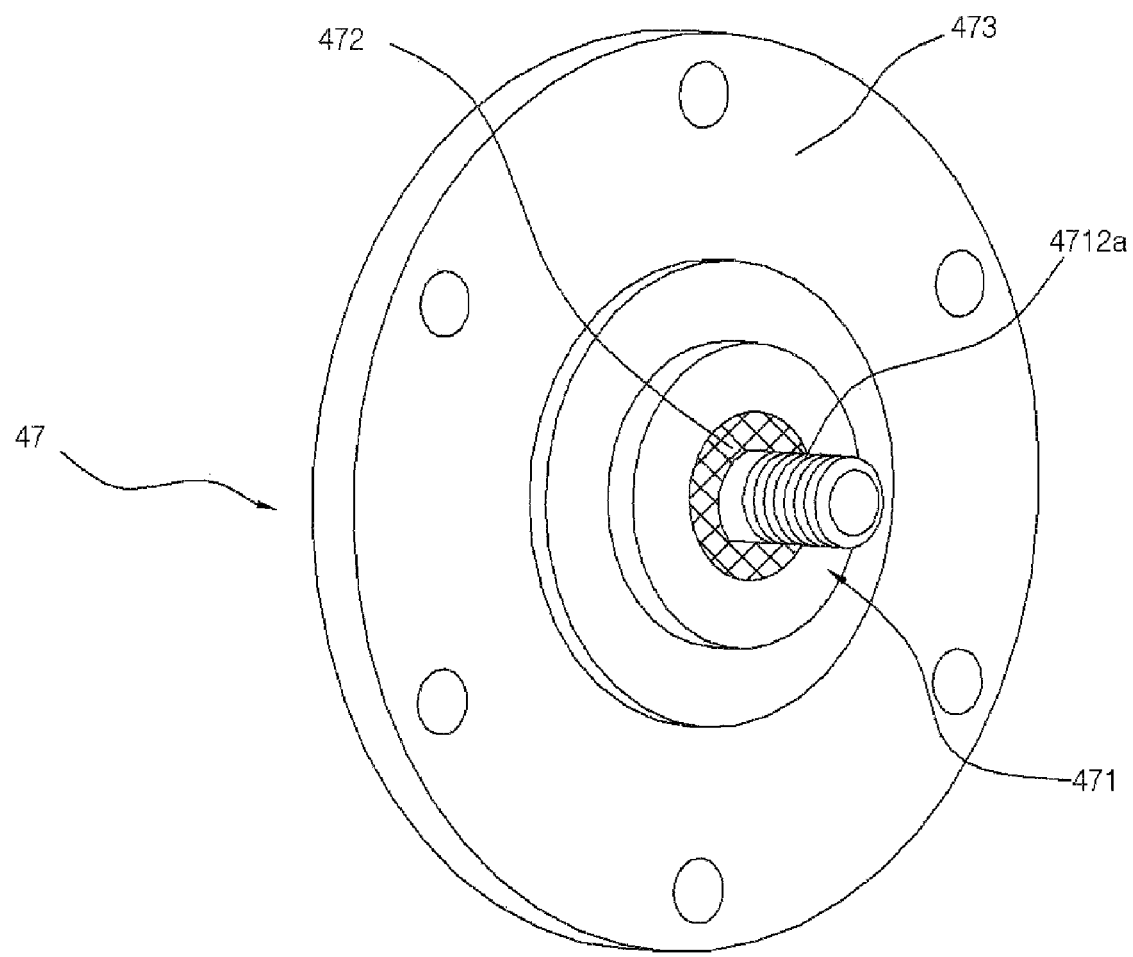
[Figure 9]

[Figure 10]
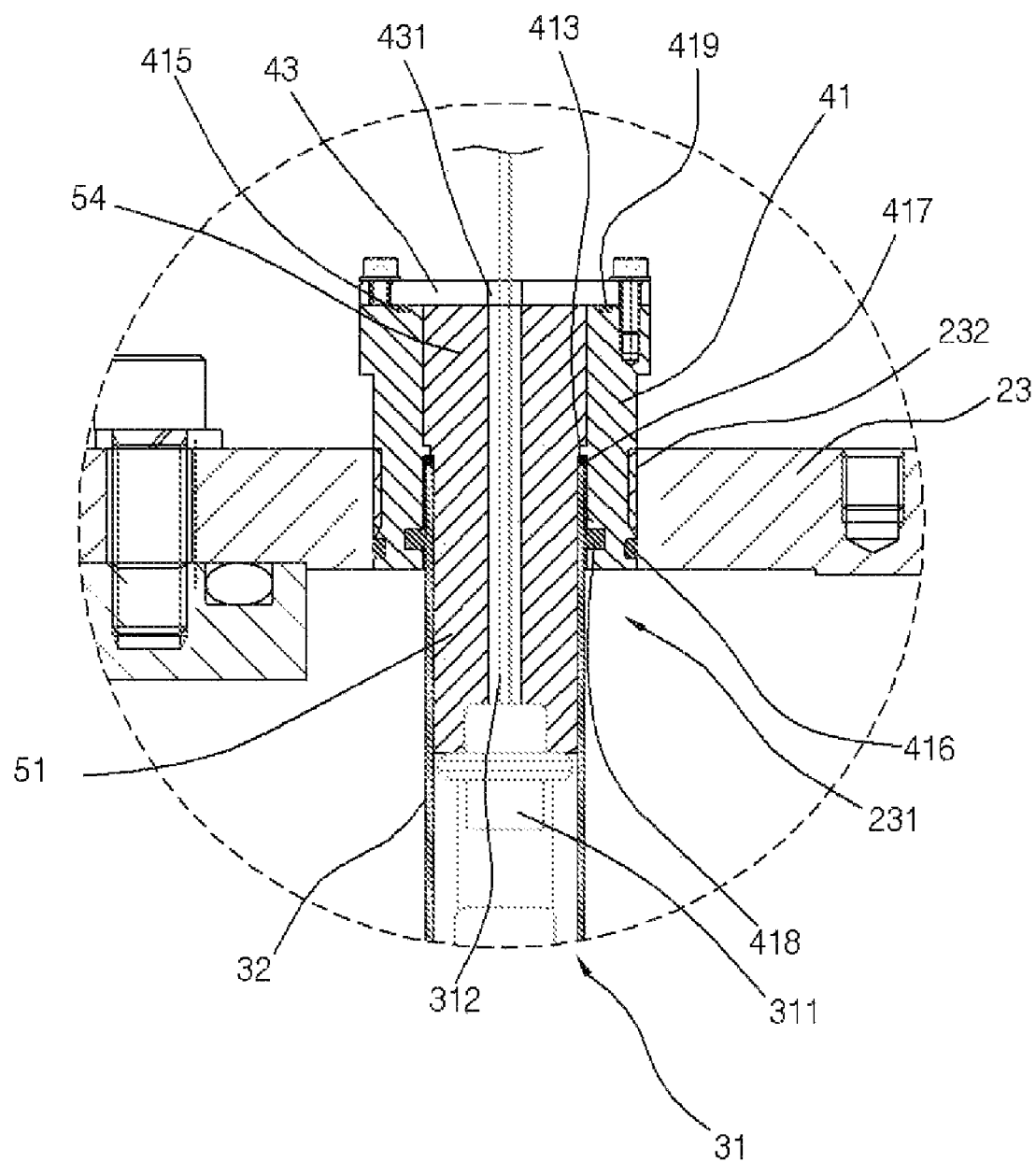

[Figure 11]
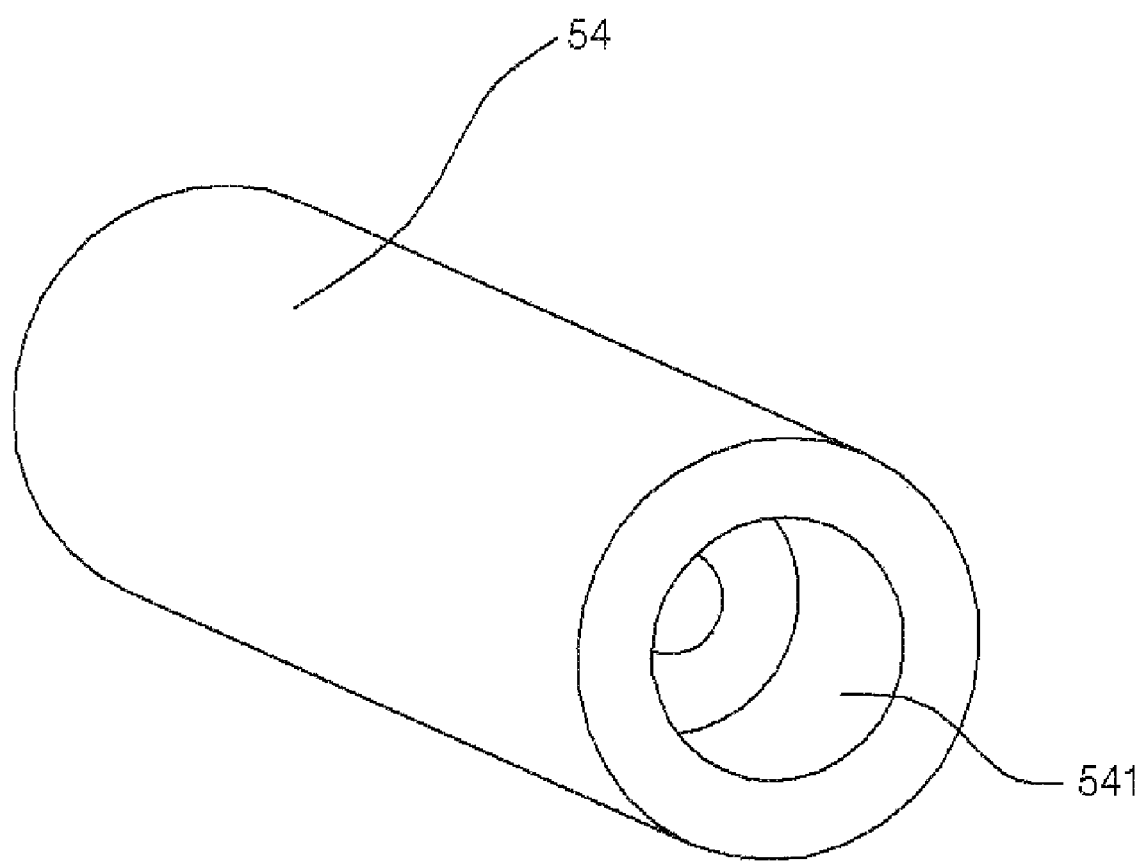

[Figure 12]
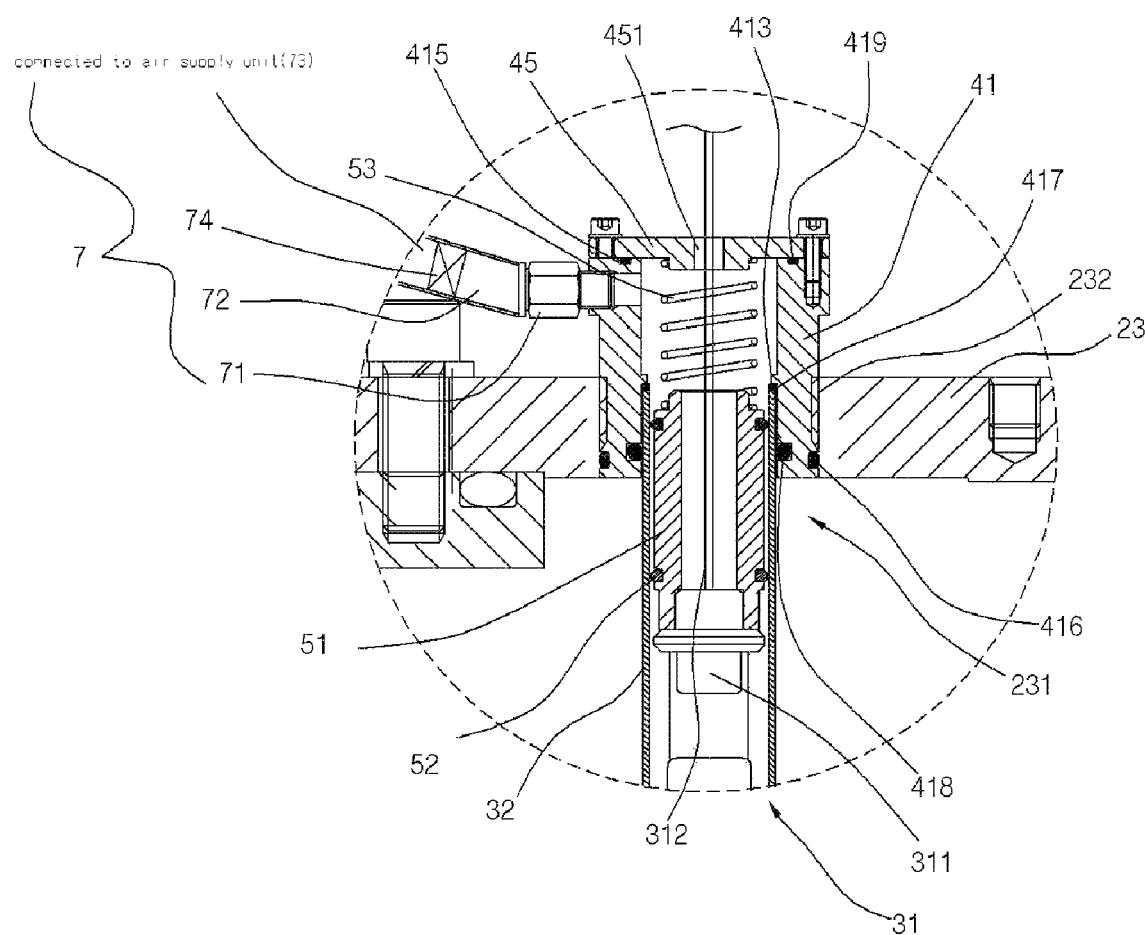

【Figure 13】
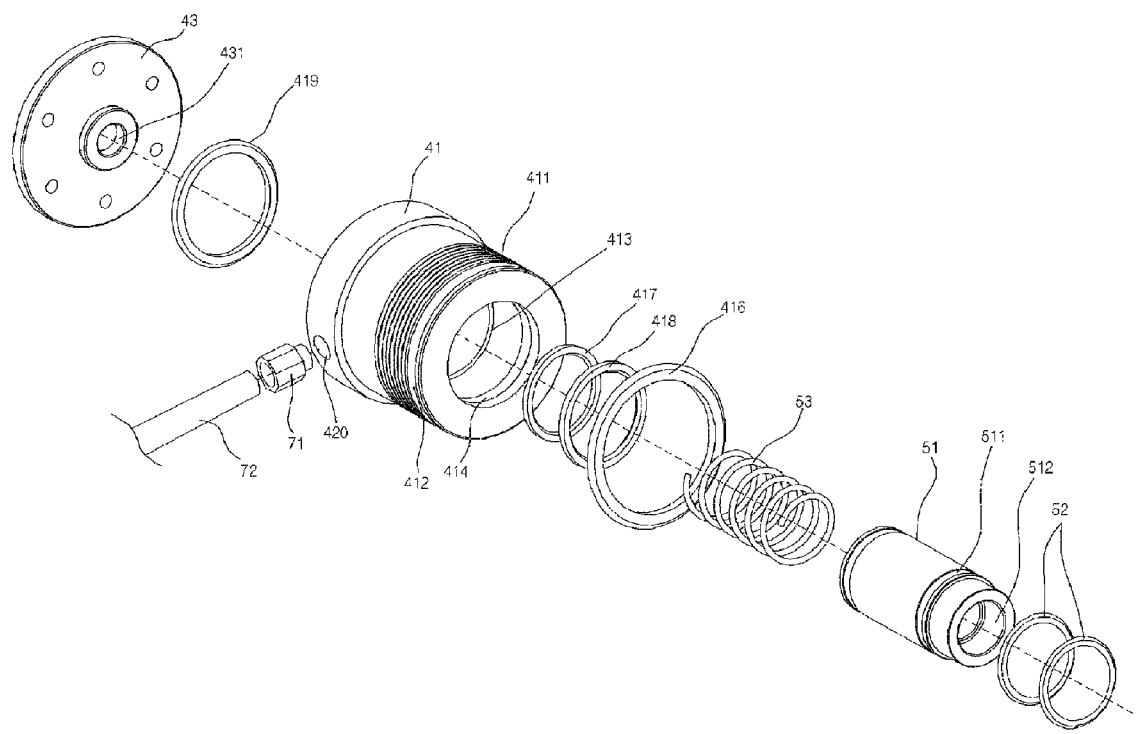

【Figure 14】
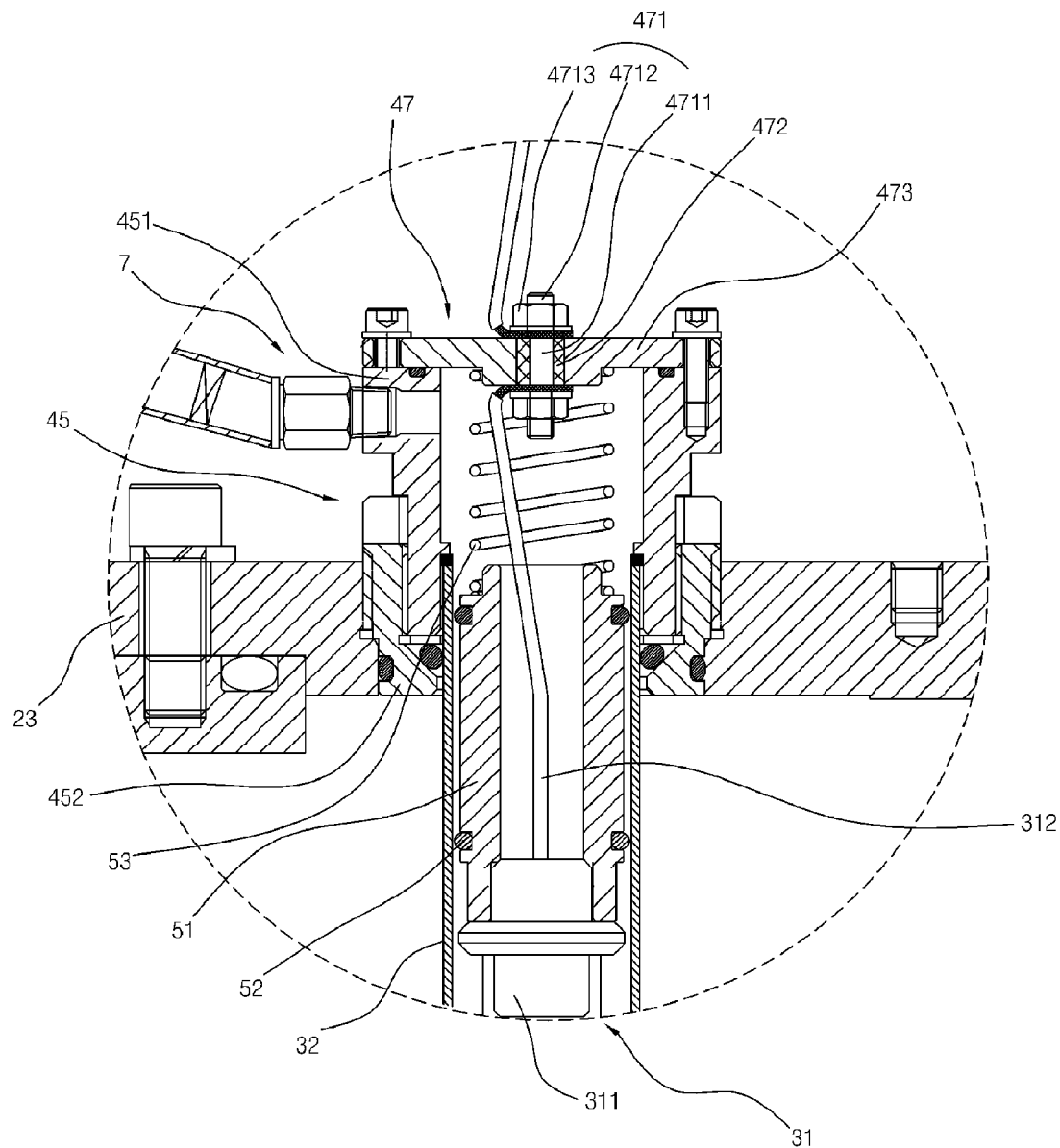

ULTRAVIOLET STERILIZER HAVING VIBRATION-PROOF FUNCTION

BACKGROUND OF THE INVENTION

1. Field of the Invention

The present invention relates generally to ultraviolet sterilizers having vibration-proof functions and, more particularly, to an ultraviolet sterilizer including an ultraviolet sterilization unit which has an inlet through which ballast water is drawn thereinto, an outlet through which the ballast water is discharged after the ballast water has been sterilized, and an ultraviolet lamp located between the inlet and the outlet, the ultraviolet lamp applying ultraviolet rays to the ballast water to sterilize the ballast water, wherein the ultraviolet sterilizer further includes a cap which supports each of the opposite ends of the ultraviolet sterilization unit, and a shock absorption unit which is elastically compressed at a first end thereof by the cap while a second end thereof elastically compresses a corresponding end of the ultraviolet lamp, whereby even if the ultraviolet sterilization unit vibrates, the sleeve pipe or the ultraviolet lamp can be prevented from being damaged, and explosive gas which may cause the ultraviolet sterilizer to explode is also prevented from entering the cap.

2. Description of the Related Art

Generally, when cargo ships sail with no cargo, ballast water is loaded in tanks of the cargo ships to keep the ships in balance. However, unfortunately, ballast water used in the cargo ships may damage native marine ecosystems because of the foreign marine creatures which have been contained in the ballast water. Therefore, it is required to treat the ballast water. To date, methods of applying ultraviolet rays to ballast water have been widely used.

FIG. 1 is a block diagram of a conventional ballast water treatment system. FIG. 2 is a sectional view showing an ultraviolet sterilizer of the conventional ballast water treatment system. In the conventional ballast water treatment system, a supply pump 11 supplies ballast water to an ultraviolet sterilizer 12, and the ultraviolet sterilizer 12 sterilizes the ballast water and discharges it into a tank 13. A control unit 14 controls the entirety of the system.

In the conventional ultraviolet sterilizer 12, a through hole is formed through a housing cover 121 to facilitate replacement of a sleeve pipe 123 and an ultraviolet lamp 124. A cap 122 is removably coupled to the through hole of the housing cover 121. The cap 122 supports the sleeve pipe 123. The ultraviolet lamp 124 is disposed in the sleeve pipe 123, and a head 1241 of the ultraviolet lamp 124 is supported by a support 125.

However, because a ship having the ultraviolet sterilizer 12 typically sails on the sea and a diesel engine which causes a lot of vibrations is used as a power source for the ship, the ultraviolet sterilizer also creates large vibrations in the longitudinal and lateral directions. Furthermore, the ultraviolet sterilizer sterilizes a large amount of ballast water at a time. Thus, excessive water pressure may be applied to the ultraviolet sterilizer. Here, the support 125 and the ultraviolet lamp 124 are not in close contact with the sleeve pipe 123, in other words, the inner surface of the sleeve pipe 123 is spaced apart from the support 125 and the ultraviolet lamp 124 by a predetermined distance. Therefore, when vibrations are applied to the ultraviolet sterilizer, the support 125 and the ultraviolet lamp 124 may excessively move in the sleeve pipe 123. Typically, the sleeve pipe 123 is made of glass, the head 1241 of the ultraviolet lamp 124 is made of ceramic, and the support 125 is also made of glass. Thus, when the ultraviolet sterilizer vibrates in the lateral direction, the support 125 or the head 1241 of the ultraviolet lamp 124 may collide with the sleeve pipe 123. Thereby, the sleeve pipe 123 or the ultraviolet lamp 124 may be damaged. In addition, when the ultraviolet sterilizer vibrates in the longitudinal direction, impacts applied to the cap 122 are directly transmitted to the ultraviolet lamp 124 through the support 125. Thereby, the support 125 collides with the head 1241 of the ultraviolet lamp 124, thus damaging the ultraviolet lamp 124 or the support 125 or the ultraviolet lamp 124.

Moreover, several devices or machines are present around the ultraviolet sterilizer. Particularly, explosive gas may be present around the ultraviolet sterilizer. If explosive gas enters the cap 122, the ultraviolet sterilizer may be exploded by a spark.

SUMMARY OF THE INVENTION

Accordingly, the present invention has been made keeping in mind the above problems occurring in the prior art, and an object of the present invention is to provide an ultraviolet sterilizer having a vibration-proof function which includes a shock absorption unit which elastically compresses an ultraviolet lamp so that even if the ultraviolet lamp is displaced by vibrations of the ultraviolet sterilizer, an ultraviolet sterilization unit can be prevented from being damaged.

Another object of the present invention is to provide an ultraviolet sterilizer in which a shock absorption member is located between a sleeve pipe and a support body of the shock absorption unit so that even if the ultraviolet lamp vibrates in the lateral direction, the ultraviolet lamp can be prevented from directly colliding with the sleeve pipe.

A still further object of the present invention is to provide an ultraviolet sterilizer which includes an elastic member which elastically compresses a corresponding end of the support body so that even if the ultraviolet lamp vibrates in the longitudinal direction, damage to the ultraviolet lamp can be prevented.

A still further object of the present invention is to provide an ultraviolet sterilizer which includes a pressure controller which supplies air into a cap to maintain the internal pressure of the cap higher than the external pressure, so that explosive gas can be prevented from entering the cap, thus preventing the explosive gas from causing the ultraviolet sterilizer to explode.

A still further object of the present invention is to provide an ultraviolet sterilizer which includes the cap having a watertight function, so that even if the ultraviolet sterilization unit is damaged, ballast water can be prevented from entering a reception space which is formed outside the cap and contains several devices belonging to the ultraviolet sterilizer.

A still further object of the present invention is to provide an ultraviolet sterilizer in which an upper body of the cap is removably coupled by screwing to a lower body of the cap such that only the upper body of the cap is separated from the ultraviolet sterilizer, so that a through hole to which the cap is coupled can be opened while the ultraviolet sterilization unit is still fastened to the housing of the ultraviolet sterilizer and, thus, some parts of the ultraviolet sterilization unit can be easily replaced with new ones without removing the entirety of the ultraviolet sterilization unit.

In order to accomplish the above object, the present invention provides an ultraviolet sterilizer having a vibration-proof function, including: an ultraviolet sterilization unit having an inlet through which ballast water is drawn thereinto, an outlet through which the ballast water is discharged therefrom after the ballast water has been sterilized, and an ultraviolet lamp located between the inlet and the outlet, the ultraviolet lamp applying ultraviolet rays to the ballast water to sterilize the ballast water; a cap supporting each of opposite ends of the ultraviolet sterilization unit; and a shock absorption unit having a first end elastically compressed by the cap, and a second end elastically compressing a corresponding end of the ultraviolet lamp, whereby the ultraviolet lamp is prevented from being damaged by a vibration.

The ultraviolet sterilization unit may further have a sleeve pipe enclosing the ultraviolet lamp to protect the ultraviolet lamp, the sleeve pipe being supported at a corresponding end thereof by the cap.

The shock absorption unit may comprise an elastic body coupled to the ultraviolet lamp, the elastic body elastically compressing an inner circumferential surface of the sleeve pipe.

The elastic body may have a hollow hole through which a lead wire passes, and an insulation layer may be formed around the hollow hole on the elastic body.

The shock absorption unit may include: a support body coupled to the ultraviolet lamp; and an elastic member having a first end elastically compressed by the cap, and a second end elastically compressing the corresponding end of the ultraviolet lamp.

The ultraviolet sterilizer may further include a shock absorption member interposed between an outer circumferential surface of the support body and the inner circumferential surface of the sleeve pipe, the shock absorption member being elastically compressed therebetween.

The cap may comprises a watertight shock-absorber located between an inner surface of the cap and an outer surface of the sleeve pipe, the watertight shock-absorber supporting the sleeve pipe in the cap and absorbing lateral vibrations of the sleeve pipe; a stop protrusion provided around the inner surface of the cap; and a shock absorption member located between an upper end of the sleeve pipe and a lower surface of the stop protrusion, the shock absorption member absorbing longitudinal vibrations of the sleeve pipe.

Furthermore, an outermost diameter of the ultraviolet lamp may be less than a diameter of the outer circumferential surface of the support body.

The ultraviolet sterilizer may further include a pressure controller connected to a predetermined portion of the cap, the pressure controller supplying air into the cap such that an internal pressure of the cap is maintained higher than an external pressure thereof.

The cap may have an air inlet hole formed through the predetermined portion of the cap. The pressure controller may include: a connector coupled to the air inlet hole; an air supply tube connected at a first end thereof to the connector; and an air supply unit connected to a second end of the air supply tube, the air supply unit generating air pressure to supply air into the air supply tube.

The pressure controller may further include a backflow prevention valve provided at a predetermined position in the air supply tube to prevent ballast water from flowing backwards from the cap towards the air supply unit.

As described above, the ultraviolet sterilizer of the present invention includes a shock absorption unit which elastically compresses an ultraviolet lamp. Thus, even if the ultraviolet lamp is moved by vibrations of the ultraviolet sterilizer, an ultraviolet sterilization unit can be prevented from being damaged.

Furthermore, a shock absorption member is located between a sleeve pipe and a support body of the shock absorption unit. Therefore, even if the ultraviolet lamp vibrates in the lateral direction, the ultraviolet lamp can be prevented from directly colliding with the sleeve pipe.

In addition, an elastic member elastically compresses a corresponding end of the support body so that even if the ultraviolet lamp vibrates in the longitudinal direction, the ultraviolet lamp can be prevented from being damaged.

The ultraviolet sterilizer further includes a pressure controller which supplies air into a cap to maintain the internal pressure of the cap higher than the external pressure, so that explosive gas can be prevented from entering the cap, thus preventing the explosive gas from causing the ultraviolet sterilizer to explode.

Furthermore, the cap has a watertight function. Hence, even if the ultraviolet sterilization unit is damaged, ballast water can be prevented from entering a reception space which is formed outside the cap and contains several devices belonging to the ultraviolet sterilizer.

In addition, an upper body of the cap is removably coupled to a lower body of the cap by screwing such that only the upper body of the cap is separated from the ultraviolet sterilizer. Therefore, a through hole to which the cap is coupled can be opened with the ultraviolet sterilization unit still fastened to the housing of the ultraviolet sterilizer. Thus, some parts of the ultraviolet sterilization unit can be easily replaced with new ones without removing the entirety of the ultraviolet sterilization unit.

BRIEF DESCRIPTION OF THE DRAWINGS

The above and other objects, features and advantages of the present invention will be more clearly understood from the following detailed description taken in conjunction with the accompanying drawings, in which:

FIG. 1 is a block diagram of a conventional ballast water treatment system;

FIG. 2 is a sectional view showing an ultraviolet sterilizer of the conventional ballast water treatment system;

FIG. 3 is a partially broken perspective view of an ultraviolet sterilizer, according to a first embodiment of the present invention;

FIG. 4 is a sectional view of the ultraviolet sterilizer according to the first embodiment of the present invention;

FIG. 5 is an enlarged view of the circled portion A of FIG. 4 according to the first embodiment of the present invention;

FIG. 6 is an exploded perspective view showing a cap and a shock absorption unit according to the first embodiment of the present invention;

FIG. 7 is an enlarged view showing the circled portion A of FIG. 4 according to a second embodiment of the present invention;

FIG. 8 is an enlarged view showing the circled portion A of FIG. 4 according to a third embodiment of the present invention;

FIG. 9 is an exploded perspective view of a cap cover according to the third embodiment of the present invention;

FIG. 10 is an enlarged view showing the circled portion A of FIG. 4 according to a fourth embodiment of the present invention;

FIG. 11 is an exploded perspective view of an elastic body according to the fourth embodiment of the present invention;

FIG. 12 is an enlarged view showing the circled portion A of FIG. 4 according to a fifth embodiment of the present invention;

FIG. 13 is an exploded perspective view showing a cap and a shock absorption unit according to the fifth embodiment of the present invention; and FIG. 14 is an enlarged view showing the circled portion A of FIG. 4 according to a sixth embodiment of the present invention.

DESCRIPTION OF THE PREFERRED EMBODIMENTS

Hereinafter, an ultraviolet sterilizer having a vibration-proof function of the present invention will be described in detail with reference to the attached drawings. Reference now should be made to the drawings, in which the same reference numerals are used throughout the different drawings to designate the same or similar components. In the following description, when it was determined that a detailed description of the conventional function and conventional structure would confuse the gist of the present invention, such description may have been omitted.

FIG. 3 is a partially broken perspective view of an ultraviolet sterilizer, according to a first embodiment of the present invention. FIG. 4 is a sectional view of the ultraviolet sterilizer according to the first embodiment of the present invention. FIG. 5 is an enlarged view of the circled portion A of FIG. 4 according to the first embodiment of the present invention. FIG. 6 is an exploded perspective view showing a cap and a shock absorption unit according to the first embodiment of the present invention. FIG. 7 is an enlarged view showing the circled portion A of FIG. 4 according to a second embodiment of the present invention. FIG. 8 is an enlarged view showing the circled portion A of FIG. 4 according to a third embodiment of the present invention. FIG. 9 is an exploded perspective view of a cap cover according to the third embodiment of the present invention. FIG. 10 is an enlarged view showing the circled portion A of FIG. 4 according to a fourth embodiment of the present invention. FIG. 11 is an exploded perspective view of an elastic body according to the fourth embodiment of the present invention. FIG. 12 is an enlarged view showing the circled portion A of FIG. 4 according to a fifth embodiment of the present invention. FIG. 13 is an exploded perspective view showing a cap and a shock absorption unit according to the fifth embodiment of the present invention. FIG. 14 is an enlarged view showing the circled portion A of FIG. 4 according to a sixth embodiment of the present invention.

Referring to FIGS. 3 through 6, the ultraviolet sterilizer having a vibration-proof function according to the first embodiment of the present invention includes a housing 2, an ultraviolet sterilization unit 3, caps 4, shock absorption units 5 and a cleaning unit 6.

The housing 2 constitutes the main body of the ultraviolet sterilizer and has a predetermined shape, preferably, a cylindrical shape which is open on the upper and lower ends thereof. Furthermore, the housing 2 has, in a sidewall thereof, an inlet 21 through which ballast water is drawn into the housing 2, and an outlet 22 through which ballast water treated by ultraviolet-sterilizing are discharged from the housing 2. Housing covers 23 are respectively removably coupled to the upper and lower parts of the housing 2 by screwing or the like. The reason that the inlet 21 and the outlet 22 are formed through the sidewalls of the housing 2 is that the efficiency which ballast water passing through the ultraviolet sterilization unit 3 is sterilized can be enhanced.

The housing covers 23 respectively covering the upper and lower parts of the housing 2 are removably coupled to the housing 2 by screwing or the like. Through holes 231 are formed through each housing cover 23 so that the ultraviolet sterilization unit 3 can be inserted into or removed from the housing 2 through the through holes 231 without opening the housing cover 23. The number of through holes 231 corresponds to the number of ultraviolet lamps 31. An internal thread 232 is formed on an inner surface of each through hole 231. Each through hole 231 is covered with the cap 4 which will be explained later herein. The principle of covering the through hole 231 with the cap 4 will be described in detail later.

The ultraviolet sterilization unit 3 applies ultraviolet rays to ballast water that flows through the housing 2 so as to sterilize the ballast water. The ultraviolet sterilization unit 3 includes ultraviolet lamps 31 and sleeve pipes 32.

The ultraviolet lamps 31 are located in the housing 2 and each ultraviolet lamp 31 emits ultraviolet rays and is in the shape of a rod or bar. It is desirable that the ultraviolet lamps 31 be oriented parallel to the axis of the cylindrical housing 2 along the longitudinal direction of the housing 2 and be arranged around the axis housing 2 at positions spaced apart from each other by a regular interval. Thus, ballast water flowing through the inlet 21 and out the outlet 22 passes through space among the ultraviolet lamps 31 in the direction perpendicular to the ultraviolet lamps 31. A head 311 made of material such as a ceramic is coupled to each of both ends of the ultraviolet lamp 31. A lead wire 312 is connected to the ultraviolet lamp 31 by the head 311 so that power is supplied to the ultraviolet lamp 31 through the lead wire 312.

The sleeve pipe 32 encloses the ultraviolet lamp 31 to protect the ultraviolet lamp 31. If impurities are attached to the surface of the sleeve pipe 32, the intensity of ultraviolet rays emitted from the ultraviolet lamp 31 may be reduced. Therefore, the surface of the sleeve pipe 32 is cleaned by the cleaning unit 6 which will be explained later. Preferably, a pipe made of quartz is used as the sleeve pipe 32.

Sterilization of ballast water is performed when the ship sails, and a large amount of ballast water must be sterilized at a time. Thus, excessive water pressure and large vibrations may be applied to the ultraviolet sterilization unit. Therefore, it is important that the structure that couples the ultraviolet sterilization unit to the housing be such that the ultraviolet sterilization unit can absorb impacts applied thereto. This will be explained in detail later herein.

Each cap 4 covers the corresponding through hole 231 and holds one end of the corresponding sleeve pipe 32. The cap 4 includes a cap body 41 and a cap cover 43.

The cap body 41 forms the entire body of the cap 4. The cap body 41 is removably coupled to the corresponding housing cover 23 to cover the corresponding through hole 231. Furthermore, the cap body 41 holds one end of the corresponding sleeve pipe 32. The cap body 41 has a predetermined shape, preferably, a cylindrical shape which is open on the upper and lower ends thereof. The cap body 41 includes an external thread 411, a watertight member insertion groove 412, a stop protrusion 413, a watertight absorber insertion groove 414 and a sealing member insert groove 415.

The external thread 411 is formed around an outer circumferential surface of a lower end of the cap body 41 and corresponds to the internal thread 232 of the through hole 231. Thus, the cap body 41 which has the external thread 411 corresponding to the internal thread 232 of the through hole 231 can be removably coupled to the through hole 231 of the housing cover 23 by threaded coupling.

The watertight member insertion groove 412 is formed around the outer circumferential surface of the cap body 41 below the external thread 411. A watertight member 416 is seated into the watertight member insertion groove 412. The water tight member 416 is located between the inner surface of the through hole 231 and the outer surface of the cap body 41 to ensure watertightness between the through hole 231 and the cap body 41.

The stop protrusion 413 is provided around the inner circumferential surface of the cap body 41 to restrict the sleeve pipe 32 from moving in the longitudinal direction. A shock absorption member 417 is interposed between a lower surface of the stop protrusion 413 and an upper end of the sleeve pipe 32 to absorb longitudinal vibrations of the sleeve pipe 32.

The watertight absorber insertion groove 414 is formed around the inner circumferential surface of the cap body 41 below the stop protrusion 413. A watertight shock-absorber 418 is seated into the watertight absorber insertion groove 414. The watertight shock-absorber 418 is disposed between the inner surface of the cap body 41 and the outer surface of the sleeve pipe 32 to ensure watertightness between the cap body 41 and the sleeve pipe 32 and absorb lateral vibrations of the sleeve pipe 32. Furthermore, the watertight shock-absorber 418 firmly holds the outer surface of the sleeve pipe 32 such that the sleeve pipe 32 is reliably retained in the housing 2.

The sealing member insert groove 415 is formed in an upper surface of the cap body 41 in an annular shape. A sealing member 419 is seated into the sealing member insert groove 415 and located between the upper surface of the cap body 41 and a lower surface of the cap cover 43 to ensure that a watertight seal is formed between the cap body 41 and the cap cover 43.

For example, O-rings can be used as the watertight member 416, the shock absorption member 417, the watertight shock-absorber 418 and the sealing member 419.

The cap cover 43 covers the upper end of the cap body 41 and is removably coupled to the cap body 41 by screwing or the like. A passing hole 431 is formed through the cap cover 43 so that the lead wire 312 is led out of the cap 4 through the passing hole 431. The cap cover 43 has a predetermined shape and, preferably, is made of a metal disk plate.

In the embodiment, the housing covers 23 are respectively coupled to the upper and lower parts of the housing 2. Thus, the caps 4 are also disposed in the upper and lower parts of the housing 2. Each cap 4 is removably coupled to the corresponding housing cover 23 and divided into the cap body 41 and the cap cover 43. The present invention is not limited to this. For example, a structure in which a cap integrally protrudes from a housing cover must also be regarded as falling within the bounds of the present invention.

Each shock absorption unit 5 is located in the corresponding sleeve pipe 32 and the corresponding cap 4. The shock absorption unit 5 supports the corresponding ultraviolet lamp 31 and prevents the ultraviolet lamp 31 from colliding with the sleeve pipe 32. The shock absorption unit 5 includes a support body 51, a shock absorption member 52 and an elastic member 53.

The support body 51 supports the ultraviolet lamp 31 in the sleeve pipe 32. The support body 51 has a predetermined shape, preferably, a hollow cylindrical shape. The support body 51 has a shock absorption member seating groove 511 and a lamp mounting depression 512. The support body 51 can be made of, for example, synthetic resin, such as a Teflon resin, or other insulation material.

The shock absorption member seating groove 511 is formed around an outer circumferential surface of the support body 51. A shock absorption member 52 is seated into the shock absorption member seating groove 511 and disposed between the inner surface of the sleeve pipe 32 and the outer surface of the support body 51. The shock absorption member 52 functions to absorb lateral vibrations of the support body 51. As necessary, the shock absorption member seating groove 511 may comprise a plurality of shock absorption member seating grooves 511.

The lamp mounting depression 512 is formed in an inner circumferential surface of a lower end of the support body 51 at a position corresponding to the head 311 of the ultraviolet lamp 31. The lamp mounting depression 512 receives the head 311 of the ultraviolet lamp 31 so that the ultraviolet lamp 31 is reliably fastened to the support body 51. Preferably, the outermost diameter of the ultraviolet lamp 31 is less than the outer diameter of the support body 51, so that even though the ultraviolet lamp 31 vibrates in the lateral direction, the ultraviolet lamp 31 can be prevented from directly colliding with the sleeve pipe 32.

The shock absorption member 52 is seated into the shock absorption member seating groove 511 such that it is elastically compressed between the inner surface of the sleeve pipe 32 and the outer surface of the support body 51. Thus, the shock absorption member 52 reliably supports the support body 51 on the inner surface of the sleeve pipe 32 and absorbs lateral vibrations of the support body 51. In addition, the support body 51 can be prevented from colliding with the sleeve pipe 32. For example, an O-ring can be used as the shock absorption member 52.

The elastic member 53 is located between an upper end of the support body 51 and the lower surface of the cap cover 43. The elastic member 53 elastically compresses a corresponding end of the support body 51, thus preventing the support body 51 from vibrating in the longitudinal direction. For example, an elastic spring or the like can be used as the elastic member 53.

The caps 4 support the respective opposite ends of the sleeve pipe 32 on the upper and lower parts of the housing 2. Therefore, the shock absorption units 5 also support the respective opposite ends of the ultraviolet lamp 31.

The cleaning unit 6 functions to remove impurities from the surfaces of the sleeve pipes 32. The cleaning unit 6 includes wipers 61, a drive shaft 62 and a drive unit 63. The wipers 61 come into contact with the outer circumferential surfaces of the respective sleeve pipes 32. The drive shaft 62 is coupled to the wiper 61. The drive unit 63 is coupled to the drive shaft 62 to operate the drive shaft 62.

Each wiper 61 functions to remove impurities from the outer surface of the corresponding sleeve pipe 32 and, preferably, has an annular shape which encloses the entire circumference of the outer surface of the sleeve pipe 32. The wiper 61 is made of synthetic resin or synthetic rubber having heat resistance. The number of wipers 61 corresponds to the number of sleeve pipes 32. In the case where several wipers 61 are used, the wipers 61 are connected to each other by connection arms 611. The connection arms 611 are connected to the drive shaft 62.

The drive shaft 62 is connected to the wipers 61 and operates the wipers 61 to remove impurities from the outer surfaces of the sleeve pipes 32. Preferably, the drive shaft 62 is located in a central portion of the housing 2 and oriented in the direction parallel to the longitudinal axis of the housing 2. An external thread is formed on an outer circumferential surface of the drive shaft 62. One end of the drive shaft 62 is coupled to the drive unit 63.

The drive unit 63 which is coupled to the one end of the drive shaft 62 generates drive force for operating the drive shaft 62 and the wipers 61. A typical motor can be used as the drive unit 63.

Hereinafter, in the ultraviolet sterilizer having the above-mentioned construction, the principle will be described with reference to FIGS. 3 through 6 whereby the ultraviolet sterilization unit 3 can be prevented from being damaged despite a comparatively large impact having been applied to the ultraviolet sterilization unit 3 attributable to water pressure increased by vibrations of the ship or there being a sudden and rapid supply of ballast water.

First, the principle whereby damage to the sleeve pipe 32 and the ultraviolet lamp 31 is prevented even when the ultraviolet lamp 31 vibrates will be explained. The head of the ultraviolet lamp 31 is inserted into the lamp mounting depression 512 of the support body 51. Thus, the ultraviolet lamp 31 and the support body 51 integrally move. Here, even though the ultraviolet lamp 31 and the support body 51 which are integrated with each other vibrate in the lateral direction, the shock absorption member 52 which is located between the inner surface of the sleeve pipe 32 and the outer surface of the support body 51 can prevent the support body 51 and the ultraviolet lamp 31 from directly colliding with the sleeve pipe 32. Furthermore, even though the ultraviolet lamp 31 and the support body 51 which are integrated with each other vibrate in the longitudinal direction, the elastic member 53 which is disposed between the upper end of the support body 51 and the lower surface of the cap cover 43 can absorb the longitudinal vibrations of the ultraviolet lamp 31 and the support body 51. As such, because the shock absorption member 52 or the elastic member 53 can absorb the lateral or longitudinal vibrations of the ultraviolet lamp 31 and the support body 51, the ultraviolet lamp 31 or the support body 51 can be prevented from directly colliding with the sleeve pipe 32 or the cap 4. Thereby, damage to the sleeve pipe 32 or the ultraviolet lamp 31 can be prevented.

The principle of preventing the sleeve pipe 32 which vibrates from being damaged will be explained. In the present invention, the watertight shock-absorber 418 is located between the inner surface of the cap body 41 and the outer surface of the sleeve pipe 32. Therefore, even though the sleeve pipe 32 vibrates in the lateral direction, the watertight shock-absorber 418 can prevent the sleeve pipe 32 from directly colliding with the cap body 41. Furthermore, the shock absorption member 417 is located between the upper end of the sleeve pipe 32 and the lower surface of the stop protrusion 413. Hence, even though the sleeve pipe 32 vibrates in the longitudinal direction, the shock absorption member 417 can absorb the longitudinal vibrations of the sleeve pipe 32. As such, because the watertight shock-absorber 418 or the shock absorption member 417 absorbs the lateral or longitudinal vibrations the sleeve pipe 32, the sleeve pipe 32 can be prevented from directly colliding with the cap 4, thereby preventing damage to the sleeve pipe 32.

The ultraviolet sterilizer according to a second embodiment of the present invention will be described with reference to FIG. 7. The structure of a cap body of the ultraviolet sterilizer according to the second embodiment differs from the ultraviolet sterilizer of the first embodiment which has been explained with reference to FIGS. 3 through 6. Below, the differences in this structure of the cap body from that of the first embodiment will be chiefly described with reference to FIG. 7.

The cap body 45 forms a main body of the cap 4 and includes an upper cap body 451 and a lower cap body 452.

An external thread 4511 is formed around an outer circumferential surface of a lower end of the upper cap body 451. A stop protrusion 4512 is provided around an inner circumferential surface of the upper cap body 451 to restrict the sleeve pipe 32 from moving upwards past the stop protrusion 4512. A sealing member insert groove 4513 is formed in an upper surface of the upper cap body 451. A sealing member 4515 is seated into the sealing member insert groove 4513 to ensure watertightness between the upper cap body 451 and the cap cover 43. A shock absorption member 4514 is interposed between a lower surface of the stop protrusion 4512 and the upper end of the sleeve pipe 32 to absorb longitudinal vibrations of the sleeve pipe 32.

The lower cap body 452 has, around an outer circumferential surface of a lower end thereof, an external thread 4521 corresponding to the internal thread 232 of the through hole 231. A watertight member insertion groove 4522 is formed around the outer circumferential surface of the lower cap body 452 below the external thread 4521. A watertight member 4525 is seated into the watertight member insertion groove 4522 to ensure watertightness between the through hole 231 and the lower cap body 452. A stop protrusion 4523 is provided around an inner circumferential surface of the lower end of the lower cap body 452. A watertight shock-absorber 4526 is interposed between the stop protrusion 4523 and the lower end of the upper cap body 451 to stably support the sleeve pipe 32 and absorb lateral vibrations of the sleeve pipe 32. In addition, the watertight shock-absorber 4526 ensures watertightness among the upper cap body 451, the lower cap body 452 and the sleeve pipe 32. Preferably, each of the watertight member 4525, the shock absorption member 4514, the watertight shock-absorber 4526 and the sealing member 4515 comprises an O-ring.

In the cap body 45 of the ultraviolet sterilizer according to the second embodiment, the upper cap body 451 is removably coupled to the lower cap body 452 by threaded coupling. Thus, only the upper cap body 451 can be separated from the housing 2 so that the through hole 231 can be open while the ultraviolet sterilization unit 3 is still fastened to the housing 2. Therefore, elements of the ultraviolet sterilization unit can be easily replaced with new ones without separating the entirety of the ultraviolet sterilization unit 3 from the housing 2.

The ultraviolet sterilizer according to a third embodiment of the present invention will be described with reference to FIGS. 8 and 9. The structure of a cap cover of the ultraviolet sterilizer according to the third embodiment differs from the ultraviolet sterilizer of the first embodiment which has been explained with reference to FIGS. 3 through 6. Below, the differences between this structure of the cap body of the third embodiment and that of the first embodiment will be chiefly described with reference to FIGS. 8 and 9.

The cap cover 47 covers the upper end of the cap body 41 and is removably coupled to the cap body 41 by screwing or the like. The cap cover 47 includes a conductor 471, an insulator 472 and a perimeter part 473.

The conductor 471 is connected to the ultraviolet lamp 31 to supply power to the ultraviolet lamp 31. For example, the conductor 471 is made of conductive material, such as copper or silver. The conductor 471 includes a conductor body 4711 which has a predetermined shape, preferably, a cylindrical shape, and wire connectors 4712 which respectively protrude from upper and lower ends of the conductor body 4711.

In detail, the upper and lower wire connectors 4712 respectively protrude from the upper and lower ends of the conductor body 4711. An external thread 4712a is formed on an outer circumferential surface of each wire connector 4712. A nut 4713 is tightened over the wire connector 4712. The lower wire connector 4712 is disposed inside the cap body 41 and connected to the lead wire 312 of the ultraviolet lamp 31. The upper wire connector 4712 is located on the outside of the cap body 41 and connected to a power supply (not shown) which supplies power to the ultraviolet lamp 31. In the embodiment, because the external thread 4712a is formed on the wire connector 4712, the lead wire 312 can be easily connected to the wire connector 4712 by the nut 4713 which is tightened over the wire connector 4712.

The insulator 472 covers an outer circumferential surface of the conductor body 4711. Preferably, the insulator 472 is made of electric insulation material, such as ceramic, synthetic resin, etc. As such, the conductor 471 is covered with the insulator 472, so that high voltage current can be prevented from being applied to portions other than the ultraviolet lamp 31.

The perimeter part 473 encloses the insulator 472 and is coupled to the upper surface of the cap 4. The perimeter part 473 can be made of various materials including metal.

The conductor 471, the insulator 472 and the perimeter part 473 are tightly integrated with each other such that a gap is prevented from being formed therebetween. For example, the conductor 471 is located inside the annular perimeter part 473 and then a material such as ceramic is deposited on the junction between the perimeter part 473 and the conductor 471, thus preventing a gap from forming therebetween.

Although it is not illustrated in this specification, a structure in which the cap cover 43 of FIGS. 8 and 9 is used in the ultraviolet sterilizer of FIG. 7 must also be regarded as falling within the bounds of the present invention.

Hereinafter the principle behind how the ultraviolet sterilizer having the above-mentioned construction can prevent ballast water from leaking out of the housing 2 even if the ultraviolet sterilization unit 3 is damaged by impurities or an accident will be described with reference to FIGS. 8 through 9.

If the sleeve pipe 32 or the ultraviolet lamp 31 of the ultraviolet sterilization unit 3 is damaged by impurities drawn into the housing 2 or an accident, ballast water which has been in the housing 2 enters the cap body 41. In the present invention, the cap cover 47 does not require a separate hole through which the lead wire 312 is led out of the cap cover 47. Furthermore, the sealing member 419 is interposed between the upper surface of the cap body 41 and the lower surface of the cap cover 47. Thus, the ballast water can be prevented from leaking out of the cap body 41. In other words, even if the ultraviolet sterilization unit 3 is damaged, ballast water which has been in the housing 2 enters only the cap 4 without leaking out of the cap 4. Therefore, the devices, such as the drive unit 63 of the cleaning unit 6, etc., can be prevented from being damaged.

The ultraviolet sterilizer according to a fourth embodiment of the present invention will be described with reference to FIGS. 10 and 11. The structure of a shock absorption unit of the ultraviolet sterilizer according to the fourth embodiment differs from the ultraviolet sterilizer of the first embodiment which has been explained with reference to FIGS. 3 through 6. Below, the differences in this structure of the shock absorption unit from that of the first embodiment will be chiefly described with reference to FIGS. 10 and 11.

The shock absorption unit 5 comprises an elastic body 54 which is coupled to the ultraviolet lamp 31 and elastically compresses the inner circumferential surface of the sleeve pipe 32.

The elastic body 54 has a predetermined shape, preferably, a hollow cylindrical shape which is open on upper and lower ends thereof. The elastic body 54 is made of viscoelastic material, such as foamed polyurethane. A lamp mounting depression 541 corresponding to the head 311 of the ultraviolet lamp 31 is formed in an inner circumferential surface of a lower end of the elastic body 54. The head 311 of the ultraviolet lamp 31 is fitted into the lamp mounting depression 541. The elastic body 54 has an outer diameter appropriate to compress the inner circumferential surface of the sleeve pipe 32. Furthermore, the length of the elastic body 54 is longer than a distance between the lower surface of the cap cover 41 and the corresponding end of the ultraviolet lamp 31 so that the elastic body 54 can elastically compress the head 311 of the ultraviolet lamp 31. Although it is not illustrated in this specification, an insulation layer made of insulation material such as ceramic may be formed around the hollow hole of the elastic body 54. The lead wire passes through the hollow hole of the elastic body 54. If an electric leakage is induced on the lead wire, electric current may be directly applied to the elastic body 54. To prevent this phenomenon, it is desirable that the insulation layer be formed on the elastic body 54.

The elastic body 54 of the present invention may be used in the ultraviolet sterilizer of FIGS. 7 through 9.

The ultraviolet sterilizer according to the fifth embodiment of the present invention will be described with reference to FIGS. 12 and 13. The ultraviolet sterilizer according to the fifth embodiment has the same general construction as that of the ultraviolet sterilizer of the first embodiment of FIGS. 3 through 6 and further includes a pressure controller 7 which is connected to a portion of the cap 4. The pressure controller 7 functions to supply air into the cap 4 such that the internal pressure of the cap 4 is maintained higher than the external pressure.

In this embodiment, an air inlet hole 420 is formed through a portion of the cap body 41.

The pressure controller 7 supplies air into the cap body through the air inlet hole 420 so that the internal pressure of the cap body 41 can be maintained higher than the external pressure. The pressure controller 7 includes a connector 71, an air supply tube 72, an air supply unit 73 and a backflow prevention valve 74.

The connector 71 connects a first end of the air supply tube 72 to the air inlet hole 420. For example, the connector 71 may comprise, for example, a nipple. The first end of the air supply tube 72 is connected to the connector 71, and a second end thereof is connected to the air supply unit 73. For example, a hose made of synthetic resin may be used as the air supply tube 72. The air supply unit 73 is connected to the air supply tube 72 and generates air pressure to supply air into the air supply tube 72. For example, a compressor or the like may be used as the air supply unit 73. The backflow prevention valve 74 is installed at a predetermined position in the air supply tube 72. Even if ballast water is drawn into the cap by a reason of, for example, an accident, the backflow prevention valve 74 can prevent the ballast water from flowing backwards, that is, towards the air supply unit 73.

Several devices or machines are present around the ultraviolet sterilizer which is installed in the ship to treat ballast water. Explosive gas may be present around the ultraviolet sterilizer. If explosive gas enters the cap 4, the ultraviolet sterilizer may explode due to a spark. Therefore, when the internal pressure of the cap body 41 is maintained higher than the external pressure by supplying air from the pressure controller 7 into the cap body 41, even if explosive gas is present around the ultraviolet sterilizer, the explosive gas can be prevented from entering the cap body 41. Therefore, explosive gas can be prevented from exploding the ultraviolet sterilizer.

Meanwhile, a structure in which the pressure controller 7 illustrated in FIGS. 12 and 13 is applied to the ultraviolet sterilizer illustrated in FIGS. 7 through 11 must also be regarded as falling within the bounds of the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An ultraviolet sterilizer having a vibration-proof function, comprising:
   a housing having an inlet through which ballast water is drawn into the housing, and an outlet through which the ballast water is discharged therefrom after the ballast water has been sterilized;
   an ultraviolet sterilization unit provided inside the housing, the ultraviolet sterilization unit including
      an ultraviolet lamp applying ultraviolet rays to the ballast water to sterilize the ballast water, and
      a sleeve pipe enclosing the ultraviolet lamp to protect the ultraviolet lamp;
   a cap supporting each of opposite ends of the ultraviolet sterilization unit, one of the ends being a corresponding end of the sleeve pipe,
   wherein the sleeve pipe is watertightly supported at the corresponding end thereof by the cap such that the ballast water is prevented from being introduced into the sleeve pipe; and
   a shock absorption unit having a first end elastically compressed by the cap and a second end elastically compressing a corresponding end of the ultraviolet lamp.

2. The ultraviolet sterilizer as set forth in claim 1, wherein the shock absorption unit comprises an elastic body coupled to the ultraviolet lamp, the elastic body elastically compressing an inner circumferential surface of the sleeve pipe.

3. The ultraviolet sterilizer as set forth in claim 2, further comprising:
   a lead wire; and
   an insulation layer,
   wherein the elastic body has a hollow hole through which the lead wire passes, and the insulation layer is formed around the hollow hole on the elastic body.

4. The ultraviolet sterilizer as set forth in claim 1, wherein the shock absorption unit comprises:
   a support body coupled to the ultraviolet lamp; and
   an elastic member having an end that is the first end, and another end that is the second end.

5. The ultraviolet sterilizer as set forth in claim 4, further comprising:
   a shock absorption member interposed between an outer circumferential surface of the support body and an inner circumferential surface of the sleeve pipe, the shock absorption member being elastically compressed therebetween.

6. The ultraviolet sterilizer as set forth in claim 5, wherein an outermost diameter of the ultraviolet lamp is less than a diameter of the outer circumferential surface of the support body.

7. An ultraviolet sterilizer having a vibration-proof function, comprising:
   an ultraviolet sterilization unit comprising:
      an inlet through which ballast water is drawn thereinto;
      an outlet through which the ballast water is discharged therefrom after the ballast water has been sterilized;
      an ultraviolet lamp located between the inlet and the outlet, the ultraviolet lamp applying ultraviolet rays to the ballast water to sterilize the ballast water; and
      a sleeve pipe enclosing the ultraviolet lamp to protect the ultraviolet lamp;
   a cap supporting each of opposite ends of the ultraviolet sterilization unit, one of the ends being an end of the sleeve, the cap comprising:
      a watertight shock-absorber located between an inner surface of the cap and an outer surface of the sleeve pipe, the watertight shock-absorber supporting the sleeve pipe in the cap and absorbing lateral vibrations of the sleeve pipe;
      a stop protrusion provided around the inner surface of the cap; and
      a shock absorption member located between an upper end of the sleeve pipe and a lower surface of the stop protrusion, the shock absorption member absorbing longitudinal vibrations of the sleeve pipe;
   a shock absorption unit having a first end elastically compressed by the cap, and a second end elastically compressing a corresponding end of the ultraviolet lamp, whereby the ultraviolet lamp is prevented from being damaged by a vibration, the shock absorption unit including
      a support body coupled to the ultraviolet lamp,
      an elastic member having an end that is the first end and another end that is the second end; and
   a shock absorption member interposed between an outer circumferential surface of the support body and the an inner circumferential surface of the sleeve pipe, the shock absorption member being elastically compressed therebetween.

8. An ultraviolet sterilizer having a vibration-proof function, comprising:
   an ultraviolet sterilization unit comprising:
      an inlet through which ballast water is drawn thereinto;
      an outlet through which the ballast water is discharged therefrom after the ballast water has been sterilized; and
      an ultraviolet lamp located between the inlet and the outlet, the ultraviolet lamp applying ultraviolet rays to the ballast water to sterilize the ballast water;
   a cap supporting each of opposite ends of the ultraviolet sterilization unit;
   a shock absorption unit having a first end elastically compressed by the cap, and a second end elastically compressing a corresponding end of the ultraviolet lamp, whereby the ultraviolet lamp is prevented from being damaged by a vibration; and
   a pressure controller connected to a predetermined portion of the cap, the pressure controller supplying air into the cap such that an internal pressure of the cap is maintained higher than an external pressure thereof.

9. The ultraviolet sterilizer as set forth in claim 8, wherein the cap has an air inlet hole formed through the predetermined portion of the cap, and
   the pressure controller comprises: a connector coupled to the air inlet hole; an air supply tube connected at a first end thereof to the connector; and an air supply unit connected to a second end of the air supply tube, the air supply unit generating air pressure to supply air into the air supply tube.

10. The ultraviolet sterilizer as set forth in claim 9, wherein the pressure controller further comprises:
   a backflow prevention valve provided at a predetermined position in the air supply tube to prevent ballast water from flowing backwards from the cap towards the air supply unit.

* * * * *